US00PP19660P2

(12) United States Plant Patent
Whetman

(10) Patent No.: US PP19,660 P2
(45) Date of Patent: Jan. 27, 2009

(54) ***DIANTHUS* PLANT NAMED 'CORAL REEF'**

(50) Latin Name: *Dianthus×hybrida*
Varietal Denomination: Coral Reef

(76) Inventor: John Whetman, Deerpark Farm, Chudleigh, Newton Abbey, Devon (GB), TQ13 0NH ( * ) Notice: Subject to any disclaimer, the term of this patent is extended or adjusted under 35 U.S.C. 154(b) by 0 days.

(21) Appl. No.: 12/008,536

(22) Filed: Jan. 14, 2008

(51) Int. Cl.
*A01H 5/00* (2006.01)

(52) U.S. Cl. ..... Plt./281

(58) Field of Classification Search ..... Plt./281, Plt./272

See application file for complete search history.

*Primary Examiner*—Annette H Para
*Assistant Examiner*—S. B. McCormick Ewoldt

(57) ABSTRACT

A new cultivar of *Dianthus* plant named 'CORAL REEF' that is characterized by pronounced compact habit, grey-green foliage, and flowers that are bright salmon pink with a pale pink edge. In combination these traits set 'CORAL REEF' apart from all other existing varieties of *Dianthus* known to the inventor.

2 Drawing Sheets

Genus: *Dianthus.*
Species:×*hybrida.*
Denomination: 'CORAL REEF'.

BACKGROUND OF THE INVENTION

This application claims the benefit of priority under 35 U.S.C. 119(f) of the application for a grant of European Community Plant Breeders Rights which was filed for the instant plant variety on Jul. 26, 2007, Application Number 2007/1687.

The present invention relates to a new and distinct cultivar of carnation that is grown for use as a flowering plant for pots and containers. The new cultivar is known botanically as *Dianthus×hybrida* and will be referred to hereinafter by the cultivar name 'CORAL REEF'.

'CORAL REEF' is a complex hybrid plant that is the product of a breeding program started by the inventor in 1985. The breeding program is ongoing, conducted in a cultivated area of Houndspool, Dawlish, Devon, United Kingdom. The primary focus of the breeding program is to produce new cultivars of carnations that exhibit unique growth habit. The inventor selected 'CORAL REEF' in 2003 for its flowers that are bright salmon pink with a pale pink edge that bloom from May through October.

'CORAL REEF' is a dwarf carnation exhibiting pronounced compact habit, grey-green foliage, and an abundance of bright salmon pink flowers. 'CORAL REEF' resulted from the open pollination between *Dianthus* 'Devon Flavia' (U.S. Plant Pat. No. 15,903) as female parent plant and an unidentified and unknown variety of *Dianthus* as male parent plant. *Dianthus* 'Flavia' is a cultivar of unknown parentage but derived from *Dianthus gratianopolitanus* (species, unpatented) and other *Dianthus* species and hybrids.

'CORAL REEF' is distinguishable from the female parent by pronounced compact habit and deeper pink flowers. *Dianthus gratianopolitanus,* also known as the Cheddar Pink, has pink flowers on a loose open plant habit.

The variety of *Dianthus* which is considered by the inventor to most closely resemble 'CORAL REEF' is *Dianthus*

'Devon Yolande' (U.S. Plant Pat. No. 16,029). 'Devon Yolande' has pale pink flowers with a darker center, but 'CORAL REEF' has a wider dark center and narrower pale margin.

Asexual reproduction of the new cultivar was first accomplished by the inventor in 2000 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'CORAL REEF'. These traits in combination distinguish this cultivar from all other commercial varieties known to the inventor. 'CORAL REEF' has not been tested under all possible conditions and phenotypic differences may be observed with variations in environmental, climatic and cultural conditions, however, without any variance in genotype.

1. *Dianthus* 'CORAL REEF' exhibits a compact habit.
2. *Dianthus* 'CORAL REEF' blooms profusely.
3. *Dianthus* 'CORAL REEF' exhibits flowers that are bright salmon pink with a pale edge from May through October.
4. *Dianthus* 'CORAL REEF' exhibits grey-green foliage.
5. At maturity, the height of the foliage mound of *Dianthus* 'CORAL REEF' is 20 cm to 30 cm; the width is 30 cm to 40 cm.
6. *Dianthus* 'CORAL REEF' is perennial and is hardy to −15° C.
7. *Dianthus* 'CORAL REEF' is suitable for use as a flowering plant in pots and containers.

BRIEF DESCRIPTION OF THE DRAWINGS

The accompanying color drawings illustrate the overall appearance of the new *Dianthus* variety 'CORAL REEF' showing colors as true as it is reasonably possible to obtain in colored reproductions of this type. Colors in the drawings may differ from the color values cited in the detailed botanical description, which accurately describe the actual colors of the new variety 'CORAL REEF'.

The drawing labeled as FIG. 1 depicts an entire flowering plant.

Figure 1:
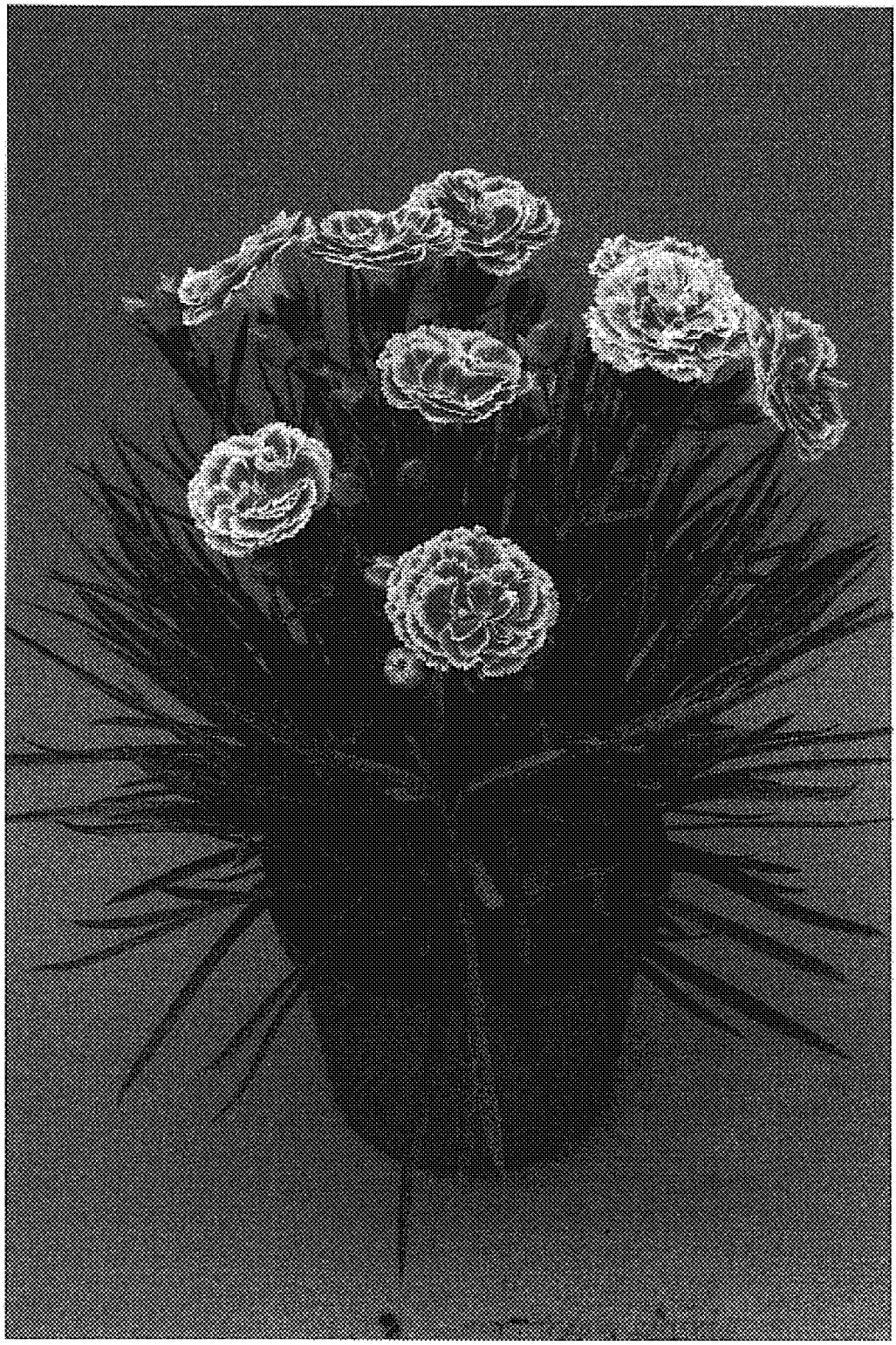
Figure 2:
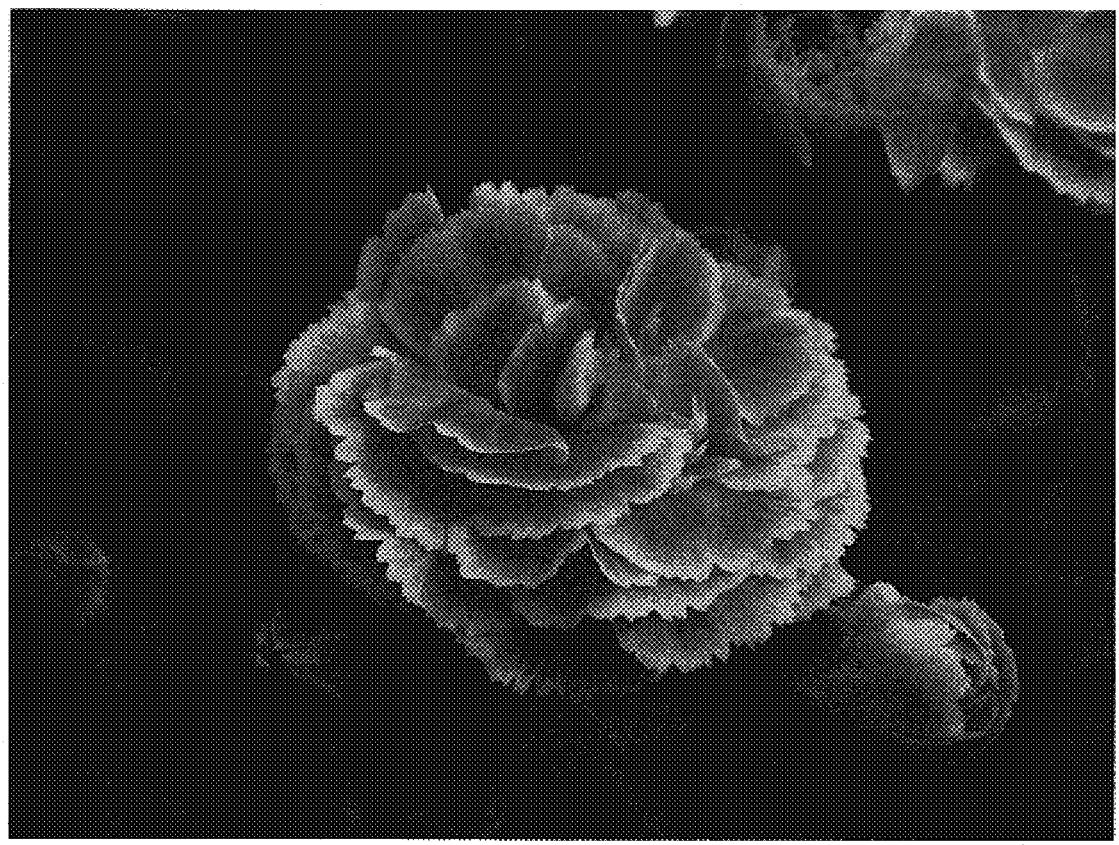

The drawing labeled as FIG. 2 depicts a close-up view of the flower. Both drawings were made from a one year old plant grown in a 1.5-liter container in an unheated glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'CORAL REEF'. Data was collected from a one year old plant grown in a 1.5-liter container in spring, and grown in an unheated glasshouse. The color determinations are in accordance with the 2002 edition of The Royal Horticultural Society Colour Chart of the Royal Horticultural Society, London, England, except where general color terms of ordinary dictionary significance are used. The colors of stems, leaves, calyx, and epicalyx have been noted on plants which retain the characteristic waxy bloom of *Dianthus.* No chemicals were used to treat the plants. Growing conditions are typical to other *Dianthus.*

Botanical classification: *Dianthus l 'CORAL REEF'.*
Species: ×*hybrida.*
Common name: Dwarf carnation.
Commercial classification: *Dianthus* hybrid.
Type: Perennial.
Use: Used as a flowering plant for pots and containers and for planting in the garden or landscape.
Parentage: 'CORAL REEF' is a complex hybrid plant that resulted from the induced open pollination between the following parent plants:
- *Female parent plant.*—*Dianthus* 'Devon Flavia', itself derived from *Dianthus gratianopolitanus* (species).
- *Male parent plant.*—Unidentified *Dianthus* hybrid.

Plant description:
- *Bloom period.*—May through October.
- *Plant habit.*—Compact mound with many branches and stems; upright growth.
- *Plant height.*—20 cm to 30 cm after 12 months.
- *Plant width.*—30 cm to 40 cm after 12 months.
- *Plant hardiness.*—Hardy to minus 15° Centigrade.
- *Root system.*—Fine fibrous roots.
- *Propagation.*—Propagation is accomplished using vegetative cuttings.
- *Cultural requirements.*—Grow in full sun, with moderate water, and well-drained moderately fertile soil. Remove dead flower heads to maintain flowering.
- *Diseases and Pests.*—Susceptible to known *Dianthus* pests and disease but no other susceptibilities to pests or disease are known to the inventor.
- *Time and temperature needed to produce a rooted cutting.*—2 weeks are needed to produce roots on cuttings using a mist propagation unit with bottom heat of 20' Centigrade, and a minimum air temperature of 15° Centigrade.
- *Crop time.*—10 weeks starting in the early spring through summer and 25 months starting in the fall is needed to produce a finished container size plant from a well-rooted cutting.

Stem:
- *Shape.*—Cylindrical.
- *Stem dimensions.*—15 cm to 20 cm in height and 3 mm in diameters.
- *Stem surface.*—Glabrous and glaucous.
- *Stem color.*—142D.
- *Branching.*—Numerous shoots from the axils of the lower leaves.
- *Internode length.*—5 mm to 10 mm between nodes.
- *Node color.*—142D.
- *Node dimensions.*—4 mm in length and 4 mm in diameter.

Foliage:
- *Type.*—Evergreen.
- *Shape.*—Linear; straight but curled upwards at tips.
- *Division.*—Simple.
- *Apex.*—Acute.
- *Base.*—Decurrent.
- *Venation.*—Not Prominent.
- *Margins.*—Entire.
- *Attachment.*—Sheathing.
- *Arrangement*—Opposite in pairs and spiraling up stem.
- *Surfaces* (*adaxial and abaxial*).—Glaucous.
- *Leaf dimensions.*—12 cm to 15 cm in length and 3 mm to 4 mm in width.
- *Leaf color* (*adaxial surfaces*).—131A.
- *Leaf color* (*abaxial surfaces*).—131B.
- *Fragrance.*—Absent.

Flowers:
- *Inflorescence.*—Cymose.
- *Number of flowers per stem.*—From 3 to 5.
- *Pedicel dimensions.*—15 cm to 20 cm in length and 3 mm to 4 mm in width.
- *Pedicel strength.*—Erect.
- *Pedicel color.*—136B.
- *Flower development.*—In sequence from the uppermost bud.
- *Flower type.*—Salviform, double and symmetrical.
- *Flower shape.*—Circular, stellate.
- *Flower profile.*—Concave, outer petals reflexed.
- *Flower length.*—(including calyx): 3 cm to 4 cm.
- *Flower diameter.*—4 cm to 5 cm.
- *Fragrance.*—Present, mildly clove-like.
- *Bud color.*—N138C.
- *Anthocyanin.*—Absent.
- *Bud dimensions.*—20 mm. in length and 6 mm. in width.
- *Bud shape.*—Rhomboid.
- *Petals.*—Persistent, apopetalous, overlapping. Number: Five petals. Margin: Serrate with indentations 1 mm to 2 mm deep. Texture: Soft. Apex: Rounded. Base: Truncate. Shape: Obdeltoid and flat. Surface: Glabrous. Dimensions: 30 mm to 40 mm in length and 15 mm to 20 mm in width. Color (adaxial surface): Ground color of blade: 48C. Band across blade: None. Edge of blade: 49C. Strap: 142C. Color (abaxial surface): Ground color of blade: 49C. Edge of blade: 49C. Band across blade: None. Strap: 142C.
- *Calyx.*—Shape: Cylindrical. Longitudinal profile: Tapered. Dimensions: 15 mm to 20 mm in length and 10 mm to 12 mm in diameter. Sepals: Fused. Number of sepals: 5. Sepal surface: Glaucous. Sepal apex: Acuminate. Sepal base: Cuneate. Sepal color (both surfaces): 136C, anthocyanin absent. Splitting: Not recorded.

*Epicalyx.*—Bracts: 2. Shape of outer lobe: Acuminate. Dimensions: 7 mm to 9 mm in length and 6 mm to 8 mm in width. Color: 136C, anthocyanin absent.

*Bracteoles.*—Number: 2. Dimensions: 5 mm to 7 mm in length and 3 mm to 4 mm in width. Color: 136C, anthocyanin absent.

*Lastingness of flower.*—Each individual flower lasts an average of 10 days at 20° C. on or off the plant.

Reproductive organs:

*Number of stamen.*—Variable, few or malformed.

*Filament color.*—White.

*Filament dimensions.*—20 mm to 25 mm in length, 0.5 mm in diameter.

*Number of anthers.*—If present, 2–5.

*Anther color.*—White.

*Anther dimensions.*—3 mm to 4 mm in length and 0.5 mm in diameter.

*Anther attachment.*—Basifixed.

*Pollen.*—Absent.

*Number of styles.*—Usually 2, occasionally 4.

*Style shoulder.*—Absent.

*Style color.*—White.

*Style dimensions.*—20 mm in length and 0.5 mm in width.

*Stigma.*—Undivided.

*Stigma color.*—49D.

*Stigma height above petals at maturity.*—2 mm to 3 mm.

*Ovary position.*—Superior.

*Ovary dimensions.*—5 mm to 6 mm in length and 5 mm to 6 mm in diameter.

*Ovary shape.*—Spindle.

*Ovary color.*—142B to 142C.

Seed: None observed.

It is claimed:

1. A new and distinct cultivar of *Dianthus* plant named 'CORAL REEF' as described and illustrated herein.

* * * * *